US012622461B2

(12) United States Patent
Lei et al.

(10) Patent No.: US 12,622,461 B2
(45) Date of Patent: May 12, 2026

(54) ATOMIZATION DEVICE

(71) Applicant: SHENZHEN SMOORE TECHNOLOGY LIMITED, Shenzhen (CN)

(72) Inventors: Guilin Lei, Shenzhen (CN); Ru Jiang, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 663 days.

(21) Appl. No.: 17/985,481

(22) Filed: Nov. 11, 2022

(65) Prior Publication Data

US 2023/0076495 A1      Mar. 9, 2023

Related U.S. Application Data

(63) Continuation of application No. PCT/CN2020/089824, filed on May 12, 2020.

(51) Int. Cl.
| | |
|---|---|
| *A24F 40/44* | (2020.01) |
| *A24F 40/10* | (2020.01) |
| *A24F 40/46* | (2020.01) |
| *A24F 40/48* | (2020.01) |
| *A61M 11/04* | (2006.01) |

(52) U.S. Cl.
CPC .............. *A24F 40/44* (2020.01); *A24F 40/10* (2020.01); *A24F 40/46* (2020.01); *A24F 40/48* (2020.01); *A61M 11/041* (2013.01); *H05B 2203/021* (2013.01)

(58) Field of Classification Search
None
See application file for complete search history.

(56) References Cited

U.S. PATENT DOCUMENTS

| | | |
|---|---|---|
| 2015/0027470 A1 | 1/2015 | Kane et al. |
| 2017/0020193 A1* | 1/2017 | Davis .................... A61M 15/06 |
| | (Continued) | |

FOREIGN PATENT DOCUMENTS

| | | |
|---|---|---|
| CN | 109310152 A | 2/2019 |
| CN | 110250576 A | 9/2019 |
| | (Continued) | |

OTHER PUBLICATIONS

CN-110613171-A, EPO english machine translation (Year: 2019).*

(Continued)

*Primary Examiner* — Michael H. Wilson
*Assistant Examiner* — Michael T Fulton
(74) *Attorney, Agent, or Firm* — Leydig, Voit & Mayer, Ltd.

(57) ABSTRACT

A vaporization device includes: an air inlet; an air outlet; a vaporization cavity in communication with the air inlet and the air outlet, a vaporization assembly being arranged in the vaporization cavity; and a first capillary liquid absorbing structure arranged on a part of the inner wall of the vaporization cavity close to the vaporization assembly. After the first capillary liquid absorbing structure absorbs an aerosol substrate, a temperature of the cavity wall of the vaporization cavity at a position where the first capillary liquid absorbing structure is located is lowerable with endothermic vaporization of the aerosol substrate.

19 Claims, 6 Drawing Sheets

(56) References Cited

U.S. PATENT DOCUMENTS

| | | | | |
|---|---|---|---|---|
| 2017/0105455 | A1 | 4/2017 | Qiu | |
| 2018/0070637 | A1 * | 3/2018 | Deng | A24F 40/485 |
| 2019/0166919 | A1 * | 6/2019 | Yilmaz | A24F 40/485 |
| 2019/0364967 | A1 * | 12/2019 | Wu | A24F 40/485 |
| 2019/0373679 | A1 * | 12/2019 | Fu | H05B 3/0019 |

FOREIGN PATENT DOCUMENTS

| | | | | | |
|---|---|---|---|---|---|
| CN | 110352017 | A | | 10/2019 | |
| CN | 110613171 | A | * | 12/2019 | |
| CN | 110613172 | A | | 12/2019 | |
| CN | 110638101 | A | | 1/2020 | |
| CN | 110638102 | A | | 1/2020 | |
| CN | 212345282 | U | | 1/2021 | |
| WO | 2018161254 | A1 | | 9/2018 | |
| WO | 2019196688 | A1 | | 10/2019 | |
| WO | WO-2019234195 | A1 | * | 12/2019 | A24F 40/10 |
| WO | 2020064921 | A1 | | 4/2020 | |

OTHER PUBLICATIONS

European Patent Office, Search Report in European Patent Application No. 20935518.9 (Jul. 6, 2023).
Patent Cooperation Treaty, International Search Report, International Application No. PCT/CN2020/089824 (Jan. 11, 2021).
Patent Cooperation Treaty, Written Opinion of the International Searching Authority, International Application No. PCT/CN2020/089824 (Jan. 11, 2021).
Chinese Patent Office, Notification of grant of patent right for invention in Chinese Patent Application No. 202010399126.6 (Jul. 22, 2024).

* cited by examiner

10

A

A

ATOMIZATION DEVICE

CROSS-REFERENCE TO PRIOR APPLICATION

This application is a continuation of International Patent Application No. PCT/CN2020/089824, filed on May 12, 2020. The entire disclosure is hereby incorporated by reference herein.

FIELD

This application relates to the field of vaporization device technologies, and in particular, to a vaporization device.

BACKGROUND

Currently, a cavity wall of a vaporization cavity in a vaporization device such as an e-cigarette is made of a plastic material. When the temperature in the vaporization cavity is excessively high, stability problems such as deformation, and even scorching of the cavity wall of the vaporization cavity are usually caused. Moreover, when the vaporization device heats and vaporizes an aerosol substrate such as e-liquid, an oil frying phenomenon is prone to occur due to uneven distribution of the aerosol substrate and high local temperature. The non-vaporized aerosol substrate splashes to the cavity wall of the vaporization cavity, or the vaporized aerosol substrate condenses on the cavity wall of the vaporization cavity. The aerosol substrate attached to the cavity wall of the vaporization cavity may reach the bottom of the vaporization device along the cavity wall, causing a liquid leakage problem.

SUMMARY

In an embodiment, the present invention provides a vaporization device, comprising: an air inlet; an air outlet; a vaporization cavity in communication with the air inlet and the air outlet, a vaporization assembly being arranged in the vaporization cavity; and a first capillary liquid absorbing structure arranged on a part of the inner wall of the vaporization cavity close to the vaporization assembly, wherein, after the first capillary liquid absorbing structure absorbs an aerosol substrate, a temperature of the cavity wall of the vaporization cavity at a position where the first capillary liquid absorbing structure is located is lowerable with endothermic vaporization of the aerosol substrate.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
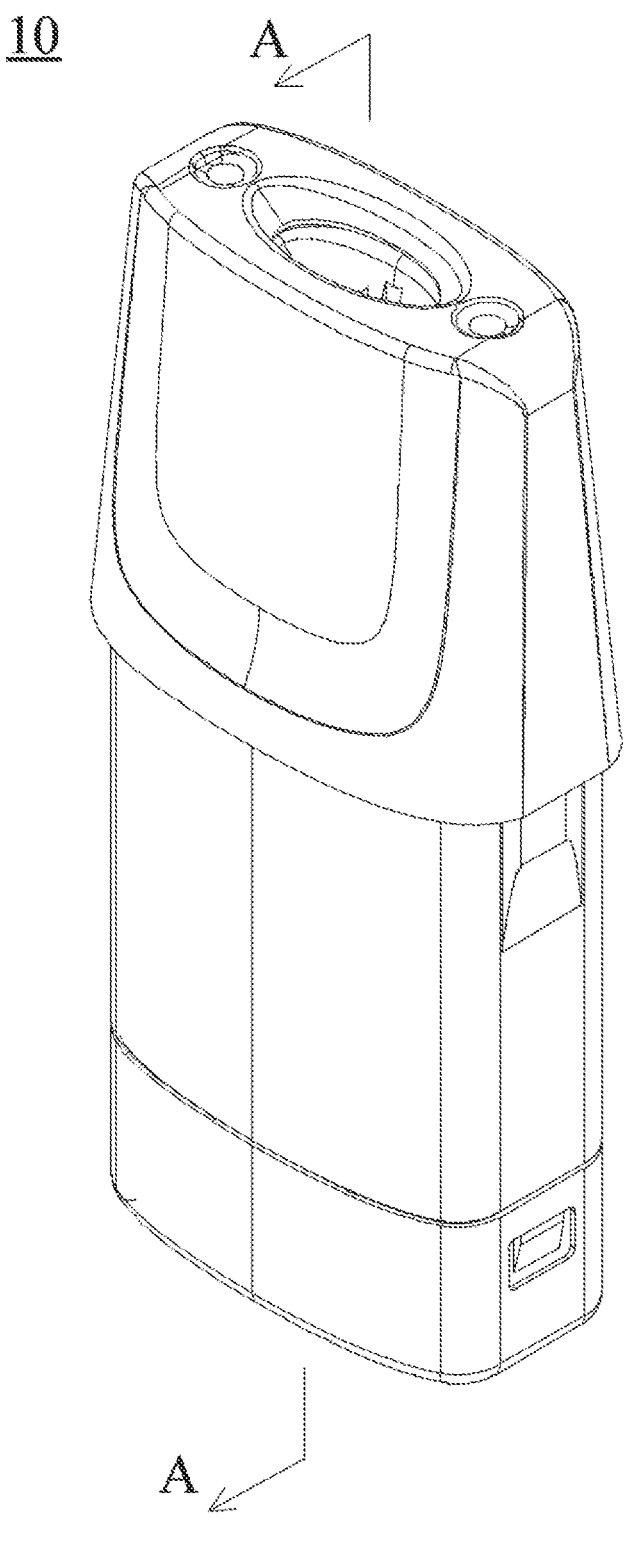
FIG. 1 is a schematic structural diagram of an embodiment of a vaporization device in this application.

In an embodiment, the present invention provides a vaporization device, which can improve the structural stability of the vaporization device and improve the anti-leakage effect of the vaporization device.

In an embodiment, the present invention provides a vaporization device. The vaporization device includes an air inlet, an air outlet, and a vaporization cavity. The vaporization cavity is in communication with the air inlet and the air outlet, and a vaporization assembly is arranged in the vaporization cavity. A first capillary liquid absorbing structure is arranged on the part of the inner wall of the vaporization cavity close to the vaporization assembly. After the first capillary liquid absorbing structure absorbs an aerosol substrate, the temperature of the cavity wall of the vaporization cavity at the position where the first capillary liquid absorbing structure is located can be lowered with endothermic vaporization of the aerosol substrate.

In an embodiment of this application, the vaporization device further includes a first carrier and a second carrier. The first carrier and the second carrier are docked to form the vaporization cavity. The air inlet is provided on the first carrier. The vaporization assembly is arranged on the second carrier, and the first capillary liquid absorbing structure is arranged on the inner wall of the second carrier.

In an embodiment of this application, the first capillary liquid absorbing structure is arranged on the side wall of the second carrier.

In an embodiment of this application, when the vaporization assembly generates heat, the temperature of the cavity wall of the vaporization cavity is less than or equal to 150° C.

In an embodiment of this application, the distance between the surface of the vaporization assembly and the inner wall of the vaporization cavity ranges from 0.5 mm to 1.8 mm.

In an embodiment of this application, the distance between the surface of the vaporization assembly and the inner wall of the vaporization cavity ranges from 1 mm to 1.5 mm.

In an embodiment of this application, the vaporization device further includes an air outlet channel. The air outlet channel is in communication with the air outlet and the vaporization cavity. A first capillary liquid absorbing structure is arranged on the part of the inner wall of the vaporization cavity connected to the inner wall of the air outlet channel, to absorb the aerosol substrate flowing back along the inner wall of the air outlet channel.

In an embodiment of this application, the first capillary liquid absorbing structure includes a first capillary groove and a second capillary groove. The first capillary groove is provided on the part of the inner wall of the vaporization cavity connected to the inner wall of the air outlet channel. The second capillary groove is far from the air outlet channel relative to the first capillary groove and a gap exists between the second capillary groove and the first capillary groove.

The aerosol substrate in the first capillary groove enters the second capillary groove after converging in the gap.

In an embodiment of this application, the widths of the first capillary groove and the second capillary groove are less than 1 mm.

In an embodiment of this application, the first capillary groove and the second capillary groove extend in a direction toward the air outlet channel.

In an embodiment of this application, the first capillary groove and the second capillary groove extend in a direction toward the air outlet.

In an embodiment of this application, a second capillary liquid absorbing structure extending to the vaporization cavity is provided on the inner wall of the air outlet channel, to guide the aerosol substrate condensing on the inner wall of the air outlet channel to the vaporization cavity.

In an embodiment of this application, a part of the second capillary liquid absorbing structure is in communication with the first capillary liquid absorbing structure arranged on the part of the inner wall of the vaporization cavity connected to the inner wall of the air outlet channel. The remaining part of the second capillary liquid absorbing structure and the first capillary liquid absorbing structure arranged on the part of the inner wall of the vaporization cavity connected to the inner wall of the air outlet channel are arranged at intervals.

In an embodiment of this application, a tapered channel is provided in the part of the vaporization cavity in communication with the air outlet channel. The cross-sectional area of the tapered channel gradually decreases in a direction close to the air outlet channel.

In an embodiment of this application, the first capillary liquid absorbing structure arranged on the part of the inner wall of the vaporization cavity connected to the inner wall of the air outlet channel is at least partially located on the inner wall of the tapered channel.

In an embodiment of this application, the vaporization assembly includes a porous heating body.

In an embodiment of this application, the porous heating body is a porous ceramic heating body.

The beneficial effect of this application is: compared with the related art, this application provides a vaporization device. The first capillary liquid absorbing structure is arranged on the part of the inner wall of the vaporization cavity of the vaporization device close to the vaporization assembly. The first capillary liquid absorbing structure is configured to absorb the aerosol substrate, and after absorbing the aerosol substrate, can lower the temperature of the cavity wall of the vaporization cavity at the position where the first capillary liquid absorbing structure is located with the endothermic vaporization of the aerosol substrate, thereby avoiding the stability problems such as deformation and scorching of the cavity wall of the vaporization cavity due to excessively high temperature, so that the structural stability of the vaporization device can be improved.

Moreover, the first capillary liquid absorbing structure in this application has functions of absorbing and storing the aerosol substrate. The aerosol substrate on the cavity wall of the vaporization cavity is at least partially locked in the first capillary liquid absorbing structure, thereby reducing the aerosol substrates accumulated in the vaporization device, and further reducing the risk of liquid leakage of the vaporization device, which is conducive to improving the anti-leakage effect of the vaporization device.

To make the objectives, technical solutions, and advantages of this application clearer, the following clearly and completely describes the technical solutions in the embodiments of this application with reference to the embodiments of this application. Apparently, the described embodiments are some rather than all of the embodiments of this application. All other embodiments obtained by a person of ordinary skill in the art based on the embodiments of this application without creative efforts shall fall within the protection scope of this application. The following embodiments and features in the embodiments may be mutually combined in a case that no conflict occurs.

To resolve the technical problem of the poor structural stability and anti-leakage effect of the vaporization device in the related art, an embodiment of this application provides a vaporization device. The vaporization device includes an air inlet, an air outlet, and a vaporization cavity. The vaporization cavity is in communication with the air inlet and the air outlet, and a vaporization assembly is arranged in the vaporization cavity. A first capillary liquid absorbing structure is arranged on the part of the inner wall of the vaporization cavity close to the vaporization assembly. After the first capillary liquid absorbing structure absorbs an aerosol substrate, the temperature of the cavity wall of the vaporization cavity at the position where the first capillary liquid absorbing structure is located can be lowered with endothermic vaporization of the aerosol substrate. Detailed descriptions are provided below.

Figure 2:
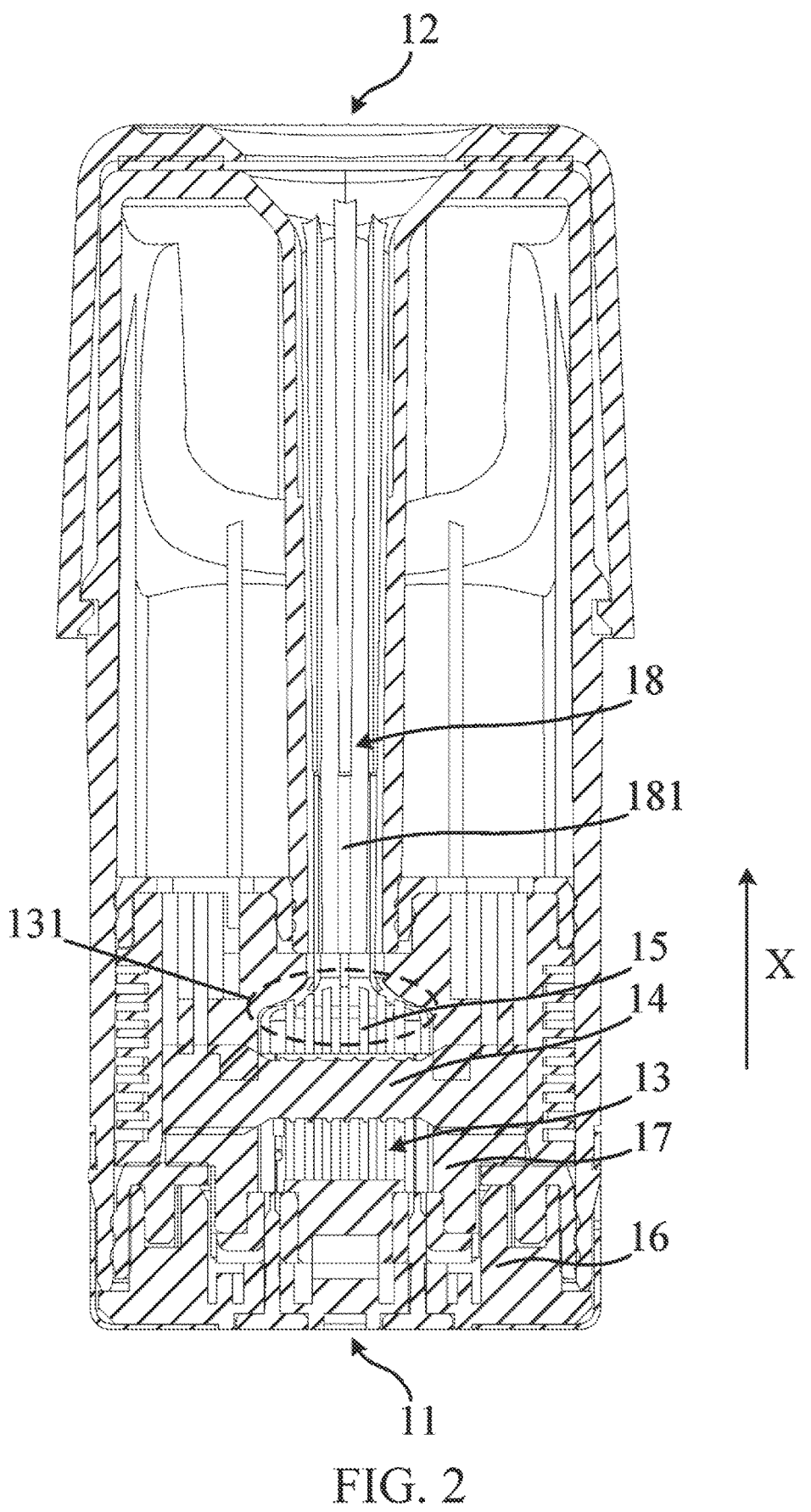
FIG. 2 is a cross-sectional view of the vaporization device shown in FIG. 1 in an A-A direction.

Referring to FIG. 1 and FIG. 2, FIG. 1 is a schematic structural diagram of an embodiment of a vaporization device in this application, and FIG. 2 is a cross-sectional view of the vaporization device shown in FIG. 1 in an A-A direction.

In an embodiment, the vaporization device 10 may be in a form such as an e-cigarette. Certainly, the vaporization device may also be a medical vaporization device applied to the medical field. A vaporization device 10 in the form of an e-cigarette is used as an example for description below. This application is not limited thereto.

Specifically, the vaporization device 10 includes an air inlet 11, an air outlet 12, and a vaporization cavity 13. The vaporization cavity 13 is in communication with the air inlet 11 and the air outlet 12, and a vaporization assembly 14 is arranged in the vaporization cavity 13. The vaporization assembly 14 is configured to vaporize an aerosol substrate (such as e-liquid and liquid medicine) in the vaporization device 10.

A position where the air inlet 11 is located is a position where air enters the vaporization device 10. When a user inhales, external air enters the vaporization cavity 13 from the air inlet 11, so that the aerosol substrate vaporized by the vaporization assembly 14 in the vaporization cavity 13 is carried to the air outlet 12 and output to the user for the user to inhale.

Optionally, the vaporization assembly 14 may be a porous heating body, which absorbs the aerosol substrate by a capillary force and generates heat to vaporize the aerosol substrate. Preferably, the vaporization assembly 14 may be a porous ceramic heating body or the like, which can be further coated with a heating film. Certainly, in other embodiments of this application, the vaporization assembly 14 may also be a design in which fiber cotton and heating wires are matched, which is not limited herein.

Considering that stability problems such as deformation and even scorching of the cavity wall of the vaporization cavity 13 are usually caused when the temperature in the vaporization cavity 13 is excessively high, in this embodiment, a first capillary liquid absorbing structure 15 is arranged on the part of the inner wall of the vaporization cavity 13 close to the vaporization assembly 14. The first capillary liquid absorbing structure 15 is configured to absorb the aerosol substrate splashing to the cavity wall of the vaporization cavity 13 due to oil frying, the aerosol substrate condensing on the cavity wall of the vaporization cavity 13, and the like.

The vaporization of the aerosol substrate requires heat absorption and the temperature of the position where the first capillary liquid absorbing structure 15 is located is high. Therefore, the aerosol substrate absorbed by the first capillary liquid absorbing structure 15 can continue to be vaporized in the first capillary liquid absorbing structure 15. In this way, after the first capillary liquid absorbing structure 15 absorbs the aerosol substrate, the aerosol substrate in the first capillary liquid absorbing structure 15 continues to be vaporized and the heat is at least partially absorbed by the aerosol substrate. Therefore, the heat of the cavity wall of the vaporization cavity 13 transferred by the vaporization assembly 14 to the position where the first capillary liquid absorbing structure 15 is located is reduced, and the heat of the cavity wall of the vaporization cavity 13 at the position where the first capillary liquid absorbing structure 15 is located is absorbed by the aerosol substrate. Then, the temperature of the cavity wall of the vaporization cavity 13 at the position where the first capillary liquid absorbing structure 15 is located is lowered. That is, the temperature of the cavity wall of the vaporization cavity 13 at the position where the first capillary liquid absorbing structure 15 is located is lowered with the endothermic vaporization of the aerosol substrate, which can avoid the stability problems such as deformation and scorching of the cavity wall of the vaporization cavity 13 due to excessively high temperature, thereby improving the structural stability of the vaporization device 10.

Certainly, that the aerosol substrate in the first capillary liquid absorbing structure 15 continues to be vaporized also means the aerosol substrate absorbed by the first capillary liquid absorbing structure 15 is reused, which can improve the utilization of the aerosol substrate of the vaporization device 10.

Optionally, in a preferred embodiment, when the vaporization assembly 14 generates heat, the temperature of the cavity wall of the vaporization cavity 13 is less than or equal to 150° C. It can be seen that, through the design of the first capillary liquid absorbing structure 15 in this embodiment, the temperature of the cavity wall of the vaporization cavity 13 can be controlled to be below 150° C., thereby effectively avoiding the stability problems such as deformation and scorching of the cavity wall of the vaporization cavity 13 due to excessively high temperature.

Further, the first capillary liquid absorbing structure 15 in this embodiment is arranged on the part of the inner wall of the vaporization cavity 13 close to the vaporization assembly 14. That is, the first capillary liquid absorbing structure 15 is arranged close to the vaporization assembly 14, which can further reduce the risk of the stability problems of the cavity wall of the vaporization cavity 13, thereby further improving the structural stability of the vaporization device 10.

Moreover, the first capillary liquid absorbing structure 15 in this embodiment has functions of absorbing and storing the aerosol substrate.

The aerosol substrate on the cavity wall of the vaporization cavity 13 is at least partially locked in the first capillary liquid absorbing structure 15, thereby reducing the aerosol substrates accumulated in the vaporization device 10, and further reducing the risk of liquid leakage of the vaporization device 10, which is conducive to improving the anti-leakage effect of the vaporization device 10. For example, for a direct-liquid vaporization device 10, more aerosol substrates are usually accumulated at the bottom of the vaporization device 10. Therefore, the first capillary liquid absorbing structure 15 in this embodiment can effectively reduce the aerosol substrates accumulated at the bottom of the vaporization device 10, thereby reducing the risk of liquid leakage of the vaporization device 10, and improving the anti-leakage effect of the vaporization device 10.

It should be noted that when the user just starts to inhale, the aerosol substrate in the vaporization assembly 14 has not been uniformly distributed, and the vaporization assembly 14 has not been uniformly heated, that is, a local overheating case exits. Therefore, an oil frying phenomenon is most likely to occur at this time. Since the temperature of the vaporization assembly 14 is low at this time, the temperature of the aerosol substrate splashing due to the oil frying is also low. Due to the low temperature, that the splashing aerosol substrate is absorbed by the first capillary liquid absorbing structure 15 does not affect the structural stability of the cavity wall of the vaporization cavity 13 at the position where the first capillary liquid absorbing structure 15 is located. Instead, a protective film can be formed at the first capillary liquid absorbing structure 15 to reduce the temperature of the cavity wall of the vaporization cavity 13 at the position where the first capillary liquid absorbing structure 15 is located with the endothermic vaporization of the aerosol substrate in the first capillary liquid absorbing structure 15, thereby avoiding the stability problems such as deformation and scorching of the cavity wall of the vaporization cavity 13 due to excessively high temperature.

Figure 3:
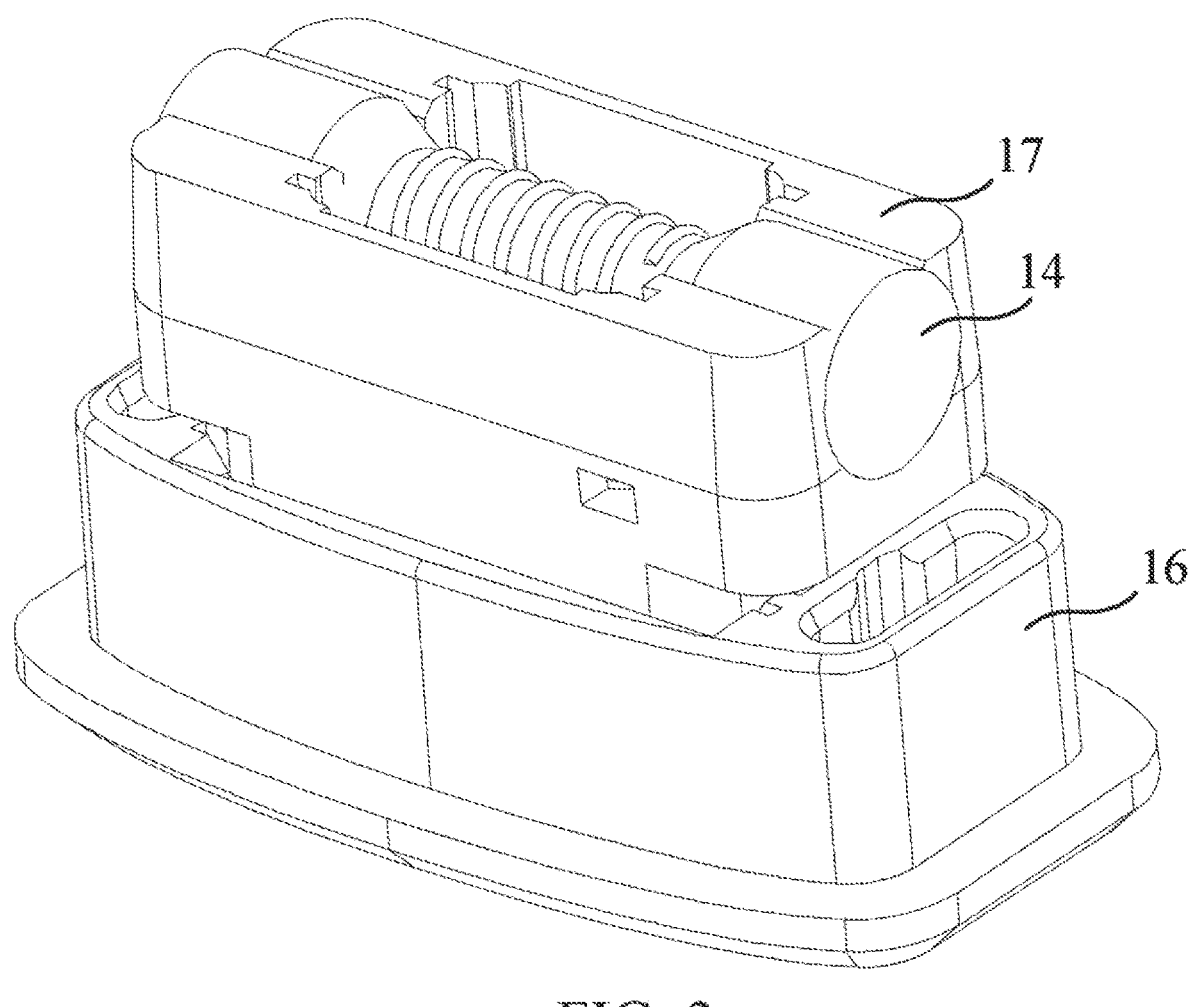
FIG. 3 is a schematic structural diagram of an embodiment of a vaporization assembly, a first carrier, and a second carrier of a vaporization device in this application.
Figure 4:
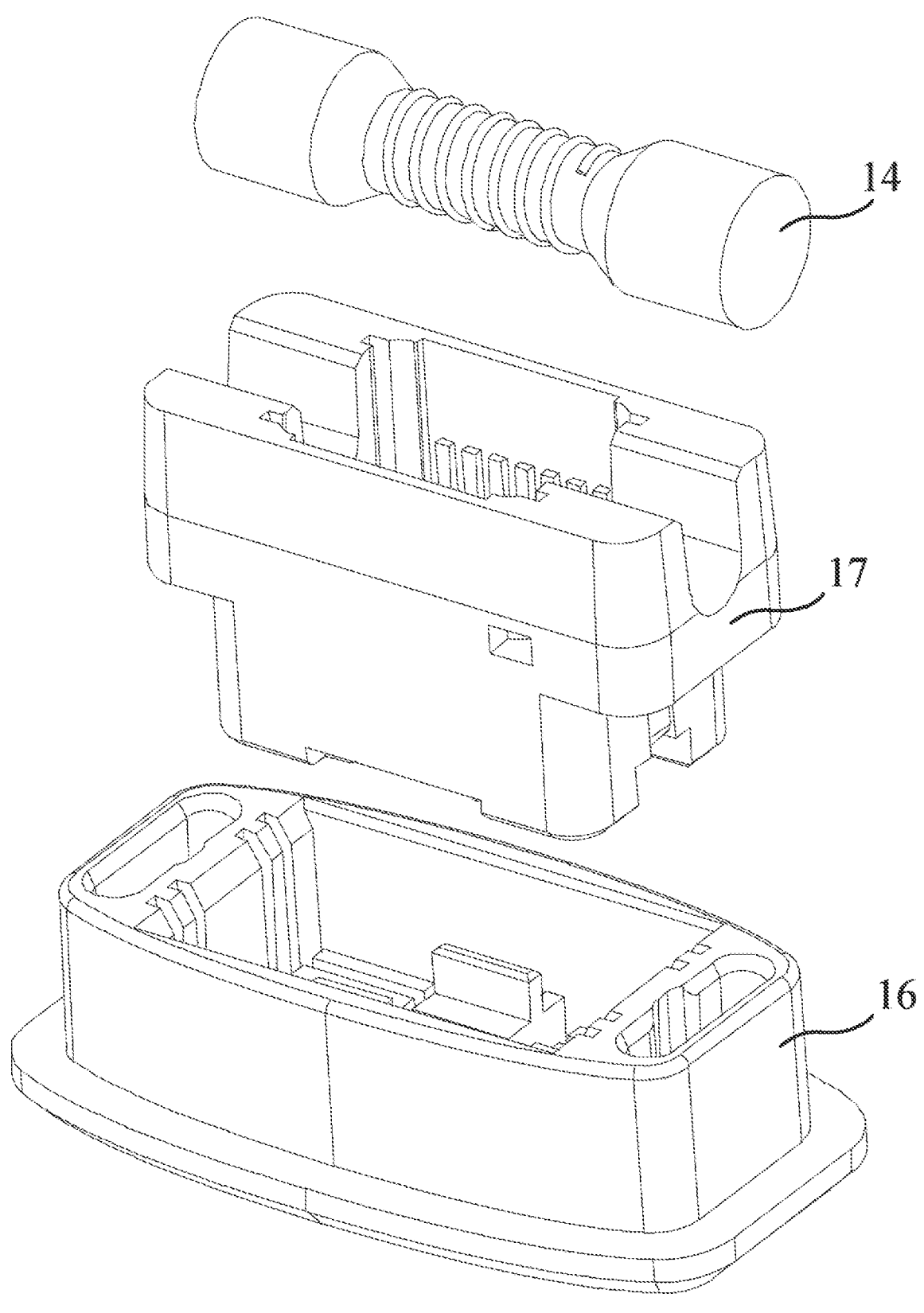
FIG. 4 is a schematic structural exploded view of the vaporization assembly, the first carrier, and the second carrier shown in FIG. 3.

Referring to FIG. 2 to FIG. 4, FIG. 3 is a schematic structural diagram of an embodiment of a vaporization assembly, a first carrier, and a second carrier of a vaporization device in this application, and FIG. 4 is a schematic structural exploded view of the vaporization assembly, the first carrier, and the second carrier shown in FIG. 3.

In an embodiment, the vaporization device 10 further includes a first carrier 16 and a second carrier 17. The first carrier 16 and the second carrier 17 are docked to form the vaporization cavity 13. The air inlet 11 is provided on the first carrier 16. The vaporization assembly 14 is arranged on the second carrier 17, and the first capillary liquid absorbing structure 15 is arranged on the inner wall of the second carrier 17. The first capillary liquid absorbing structure 15 may be arranged on the side wall or a bottom wall of the second carrier 17. FIG. 2 shows a case that the first capillary liquid absorbing structure 15 is arranged on the side wall of the second carrier 17, which is not limited herein.

Figure 5:
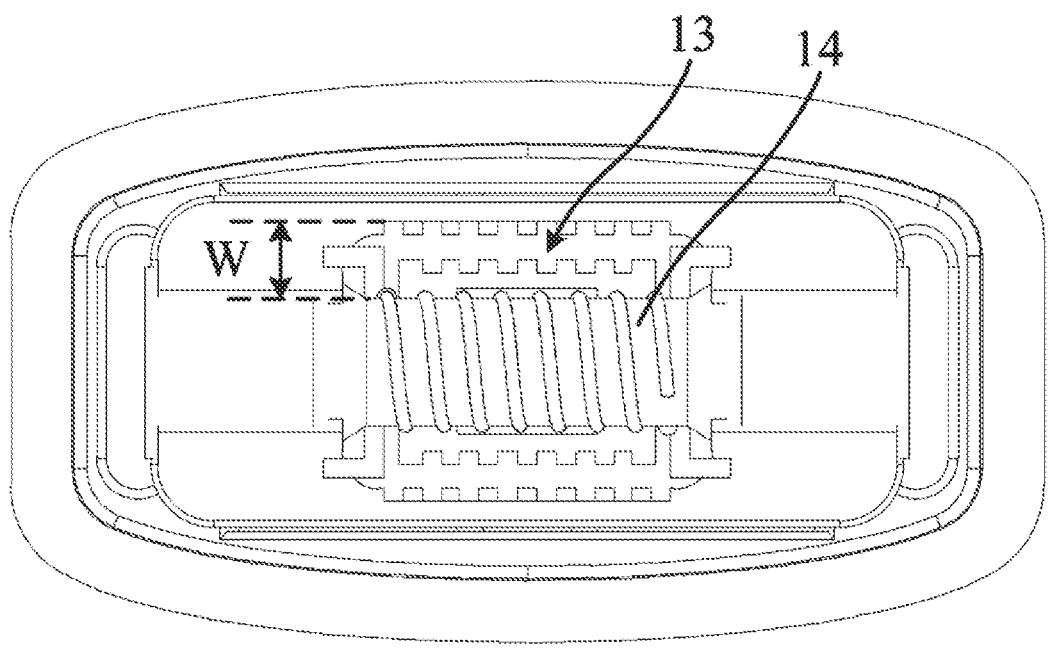
FIG. 5 is a schematic structural top view of the vaporization assembly, the first carrier, and the second carrier shown in FIG. 3.

Referring to FIG. 2 and FIG. 5, FIG. 5 is a schematic structural top view of the vaporization assembly, the first carrier, and the second carrier shown in FIG. 3.

In an embodiment, when the vaporization assembly 14 heats up to its maximum temperature of 250° C., if the first capillary liquid absorbing structure 15 is not arranged on the cavity wall of the vaporization cavity 13, the distance between the surface of the vaporization assembly 14 and the inner wall of the vaporization cavity 13 usually needs to be more than 2 mm to ensure that the cavity wall of the vaporization cavity 13 is not thermally deformed, scorched, or the like. This makes an excessively large cross-sectional area of the vaporization cavity 13, and causes an excessively low flow velocity of an airflow in the vaporization cavity 13 when the user inhales, which is not conducive for the airflow to carry the vaporized aerosol substrate for the user to inhale.

In view of this, after the first capillary liquid absorbing structure 15 is arranged on the cavity wall of the vaporization cavity 13 in this embodiment, the distance (the distance W shown in FIG. 5) between the surface of the vaporization assembly 14 and the inner wall of the vaporization cavity 13 is allowed to decrease to 0.5 mm to 1.8 mm, and then the temperature of the cavity wall of the vaporization cavity 13 is controlled to be below 150° C. Compared with a case that the first capillary liquid absorbing structure 15 is not arranged, the distance between the surface of the vaporization assembly 14 and the inner wall of the vaporization cavity 13 in this embodiment decreases, making the cross-sectional area of the vaporization cavity 13 reduced while when the user inhales, and the flow velocity of the airflow in the vaporization cavity 13 is increased. Specifically, when the user inhales, the flow velocity of the airflow in the vaporization cavity 13 is at least increased by 10%, and it can be ensured that the cavity wall of the vaporization cavity 13 is not thermally deformed, scorched, or the like. In addition, that the distance between the surface of the vaporization assembly 14 and the inner wall of the vaporization cavity 13 in this embodiment decreases means that the vaporization cavity 13 is allowed to be designed with a smaller volume, which is conducive to the miniaturization of the vaporization device 10.

Preferably, in a case that the first capillary liquid absorbing structure 15 is arranged on the cavity wall of the vaporization cavity 13 in this embodiment, the distance between the surface of the vaporization assembly 14 and the inner wall of the vaporization cavity 13 preferably ranges from 1 mm to 1.5 mm. In this way, the flow velocity of the airflow in the vaporization cavity 13 can be increased as much as possible, and it can be ensured as much as possible that the cavity wall of the vaporization cavity 13 is not thermally deformed, scorched, or the like.

Still referring to FIG. 2, in an embodiment, the vaporization device 10 further includes an air outlet channel 18. The air outlet channel 18 is in communication with the air outlet 12 and the vaporization cavity 13. Air entering the vaporization cavity 13 from the air inlet 11 is carried to the air outlet channel 18 by the aerosol substrate vaporized by the vaporization assembly 14 and output to the user along the air outlet channel 18 for the user to inhale.

Condensation may occur after the vaporized aerosol substrate contacts the inner wall of the air outlet channel 18, and the aerosol substrate condensing on the inner wall of the air outlet channel 18 may return to the vaporization cavity 13 along the air outlet channel 18. Therefore, the first capillary liquid absorbing structure 15 is arranged on the part of the inner wall of the vaporization cavity 13 connected to the inner wall of the air outlet channel 18, to absorb the aerosol substrate flowing back along the inner wall of the air outlet channel 18. In this way, the aerosol substrate condensing on the inner wall of the air outlet channel 18 may be reused and configured to form the protective film at the first capillary liquid absorbing structure 15 to control the temperature of the cavity wall of the vaporization cavity 13 (that is, reducing the temperature of the cavity wall of the vaporization cavity 13 at the position where the first capillary liquid absorbing structure 15 is located with the endothermic vaporization of the aerosol substrate in the first capillary liquid absorbing structure 15 as illustrated in the foregoing embodiment). Further, to guide the aerosol substrate condensing on the inner wall of the air outlet channel 18 to flow back to the vaporization cavity 13, a second capillary liquid absorbing structure 181 extending to the vaporization cavity 13 is provided on the inner wall of the air outlet channel 18 in this embodiment. After the second capillary liquid absorbing structure 181 absorbs the aerosol substrate condensing on the inner wall of the air outlet channel 18, the absorbed aerosol substrate is guided to the vaporization cavity 13, which is conducive to optimizing a diversion effect of the aerosol substrate on the inner wall of the air outlet channel 18.

Further, a part of the second capillary liquid absorbing structure 181 is in communication with the first capillary liquid absorbing structure 15 arranged on the part of the inner wall of the vaporization cavity 13 connected to the inner wall of the air outlet channel 18. The aerosol substrate in the part of the second capillary liquid absorbing structure 181 is guided to the first capillary liquid absorbing structure 15 to help the accumulation of the aerosol substrates in the first capillary liquid absorbing structure 15, thereby improving the structural stability of the vaporization device 10.

The remaining part of the second capillary liquid absorbing structure 181 and the first capillary liquid absorbing structure 15 arranged on the part of the inner wall of the vaporization cavity 13 connected to the inner wall of the air outlet channel 18 are arranged at intervals. That is, the remaining part of the second capillary liquid absorbing structure 181 is not in communication with the first capillary liquid absorbing structure 15. The aerosol substrate in the part of the second capillary liquid absorbing structure 181 may be directly guided to the vaporization assembly 14 to be re-vaporized by the vaporization assembly 14.

Still referring to FIG. 2, in an embodiment, a tapered channel 131 is provided in the part of the vaporization cavity 13 in communication with the air outlet channel 18. The cross-sectional area of the tapered channel 131 gradually decreases in a direction (as shown by the arrow X in FIG. 2, the same below) close to the air outlet channel 18. The first capillary liquid absorbing structure 15 arranged on the part of the inner wall of the vaporization cavity 13 connected to the inner wall of the air outlet channel 18 is at least partially located on the inner wall of the tapered channel 131.

When an oil frying phenomenon occurs, the aerosol substrate of large droplets splashing vertically in the direction close to the air outlet channel 18 returns to the vaporization assembly 14 under the action of gravity and is heated and re-vaporized. A part of the aerosol substrate of large droplets splashing around is absorbed by the first capillary liquid absorbing structure 15 on the side. There is also a part of the aerosol substrate splashing upward obliquely in the direction close to the air outlet channel 18 at a vertical upward velocity, which may be blocked by the inner wall of the tapered channel 131 and absorbed by the first capillary liquid absorbing structure 15 on the inner wall of the tapered channel 131. The aerosol substrate of small droplets driven by the airflow can enter the air outlet channel 18 without being affected by the tapered channel 131. In this way, the aerosol substrate of large droplets can be prevented from entering the air outlet channel 18 to be inhaled by the user, avoiding affecting the user's taste.

Moreover, when the user inhales, the airflow passes through the tapered channel 131. The cross-sectional area of the tapered channel 131 gradually decreases in the direction close to the air outlet channel 18. Therefore, the flow velocity of the airflow in the tapered channel 131 is increased, which helps the vaporized aerosol substrate to be carried and output to the user by the airflow, and further alleviates the condensation of the vaporized aerosol substrate.

Figure 6:
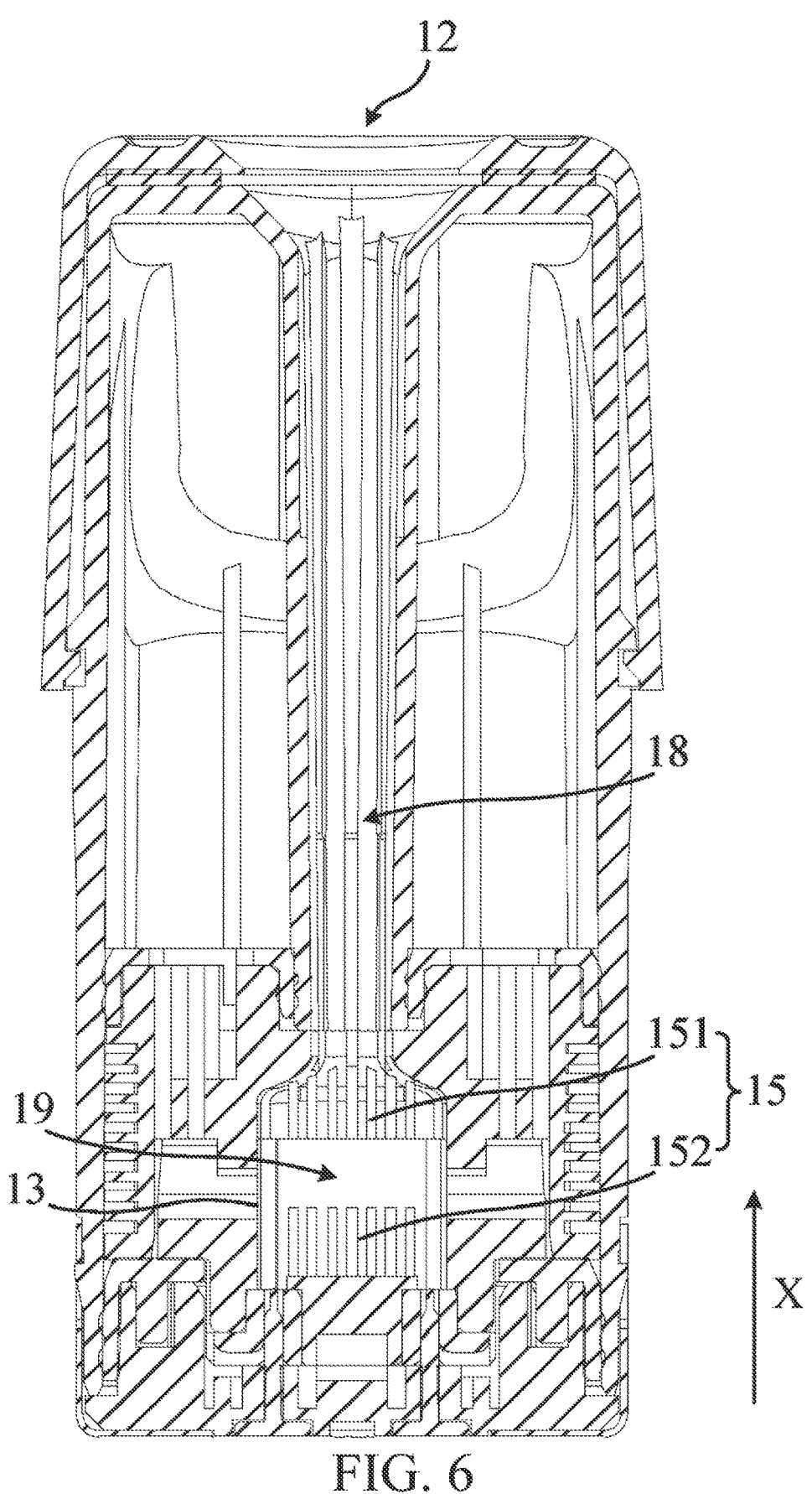
FIG. 6 is a schematic structural diagram of the vaporization device shown in FIG. 2 after the vaporization assembly is omitted.

Referring to FIG. 6, FIG. 6 is a schematic structural diagram of the vaporization device shown in FIG. 2 after the vaporization assembly is omitted.

It should be noted that, the first capillary liquid absorbing structure 15 may be a capillary groove having a capillary force or the like, which can absorb the aerosol substrate by the capillary force. Certainly, the first capillary liquid absorbing structure 15 may also be other structures having the capillary force. For example, roughening processing such as grinding is performed on a surface of the vaporization cavity 13, to form a structure having the capillary force in the form such as a frosted surface and a texture, that is, the first capillary liquid absorbing structure 15. The first capillary liquid absorbing structure 15 being the capillary groove is used as an example for description below. The type of the first capillary liquid absorbing structure 15 is not limited thereto.

In an embodiment, the first capillary liquid absorbing structure 15 includes a first capillary groove 151 and a second capillary groove 152. The first capillary groove 151 is provided on the part of the inner wall of the vaporization cavity 13 connected to the inner wall of the air outlet channel 18. The second capillary groove 152 is far from the air outlet channel 18 relative to the first capillary groove 151. A gap 19 exits between the first capillary groove 151 and the second capillary groove 152. The aerosol substrate in the first capillary groove 151 enters the second capillary groove 152 after converging in the gap 19. In this way, the aerosol substrate in the first capillary groove 151 is allowed to be mixed uniformly at the gap 19 and be uniformly distributed to the second capillary groove 152, thereby improving the uniformity of the distribution of the aerosol substrate in the first capillary liquid absorbing structure 15 on the inner wall of the vaporization cavity 13, which is conducive to reducing the risk of the structural stability problems of the cavity wall of the vaporization cavity 13.

Further, the widths of the first capillary groove 151 and the second capillary groove 152 are preferably less than 1 mm, so that the first capillary groove 151 and the second capillary groove 152 have a sufficient capillary liquid absorbing capability. If the widths of the first capillary groove 151 and the second capillary groove 152 are excessively large, the liquid absorbing capability of the first capillary groove 151 and the second capillary groove 152 may be weakened, which is insufficient for use. Moreover, a design value of the widths of the first capillary groove 151 and the second capillary groove 152 further depends on the viscosity of the aerosol substrate and a structure design constraint of the vaporization device 10. In addition, a larger depth of the capillary groove indicates a larger liquid storage capacity. Therefore, if the structure allows, increasing the depth of the capillary groove is conducive to increasing the liquid storage capacity of the first capillary groove 151 and the second capillary groove 152, thereby reducing the risk of liquid leakage.

Moreover, both the first capillary groove 151 and the second capillary groove 152 can extend in the direction close to the air outlet channel 18, that is, extending in a direction close to the air outlet 12, as shown by the arrow X in FIG. 6. Further, the first capillary groove 151 and the second capillary groove 152 are vertical grooves, which is conducive to injection molding of the first capillary groove 151 and the second capillary groove 152. Certainly, in other embodiments of this application, the first capillary groove 151 and the second capillary groove 152 may also not be vertical grooves, for example, may be implemented by a 3D printing technology.

To sum up, in the vaporization device provided by this application, the first capillary liquid absorbing structure is arranged on the part of the inner wall of the vaporization cavity close to the vaporization assembly. The first capillary liquid absorbing structure is configured to absorb the aerosol substrate, and after absorbing the aerosol substrate, can lower the temperature of the cavity wall of the vaporization cavity at the position where the first capillary liquid absorbing structure is located with the endothermic vaporization of the aerosol substrate, thereby avoiding the stability problems such as deformation and scorching of the cavity wall of the vaporization cavity due to excessively high temperature, so that the structural stability of the vaporization device can be improved.

Moreover, the first capillary liquid absorbing structure in this application has functions of absorbing and storing the aerosol substrate. The aerosol substrate on the cavity wall of the vaporization cavity is at least partially locked in the first capillary liquid absorbing structure, thereby reducing the aerosol substrates accumulated in the vaporization device, and further reducing the risk of liquid leakage of the vaporization device, which is conducive to improving the anti-leakage effect of the vaporization device.

In addition, in this application, unless otherwise explicitly specified or defined, the terms such as "connect", "connection" and "stack" should be understood in a broad sense. For example, the connection may be a fixed connection, a detachable connection, or an integral connection; or the connection may be a direct connection, an indirect connection through an intermediary, or internal communication between two components or mutual interaction relationship between two components. A person of ordinary skill in the art may understand the specific meanings of the foregoing terms in this application according to specific situations.

Finally, it should be noted that the foregoing embodiments are merely intended for describing the technical solutions of this application other than limiting this application. Although this application is described in detail with reference to the foregoing embodiments, a person of ordinary skill in the art should understand that they may still make modifications to the technical solutions described in the foregoing embodiments or make equivalent replacements to some or all technical features thereof, without departing from the scope of the technical solutions of the embodiments of this application.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A vaporization device, comprising:
a first carrier;
a second carrier;
an air inlet;
an air outlet;
a vaporization cavity in communication with the air inlet and the air outlet, a vaporization assembly being arranged in the vaporization cavity; and
a first capillary liquid absorbing structure fixedly arranged on a part of an inner wall of the vaporization cavity close to the vaporization assembly,
wherein, after the first capillary liquid absorbing structure absorbs an aerosol substrate, a temperature of the inner wall of the vaporization cavity at a position where the first capillary liquid absorbing structure is located is lowerable with endothermic vaporization of the aerosol substrate,
wherein the first carrier and the second carrier are docked to form the vaporization cavity,
wherein the air inlet is provided on the first carrier,
wherein the vaporization assembly is arranged on the second carrier, and
wherein the first capillary liquid absorbing structure is arranged on an inner wall of the second carrier.

2. The vaporization device of claim 1, wherein the first capillary liquid absorbing structure is arranged on a side wall of the second carrier.

3. The vaporization device of claim 1, wherein, when the vaporization assembly generates heat, the temperature of the inner wall of the vaporization cavity is less than or equal to 150° C.

4. The vaporization device of claim 1, wherein a distance between the surface of the vaporization assembly and the inner wall of the vaporization cavity ranges from 0.5 mm to 1.8 mm.

5. The vaporization device of claim 4, wherein the distance between the surface of the vaporization assembly and the inner wall of the vaporization cavity ranges from 1 mm to 1.5 mm.

6. The vaporization device of claim 1, further comprising an air outlet channel in communication with the air outlet and the vaporization cavity,
wherein the first capillary liquid absorbing structure is arranged on a part of the inner wall of the vaporization cavity connected to the inner wall of the air outlet channel so as to absorb the aerosol substrate flowing back along the inner wall of the air outlet channel.

7. The vaporization device of claim 6, wherein the first capillary liquid absorbing structure comprises a first capillary groove and a second capillary groove, the first capillary groove being provided on a part of the inner wall of the vaporization cavity connected to the inner wall of the air outlet channel, the second capillary groove being far from the air outlet channel relative to the first capillary groove,
wherein a gap exists between the second capillary groove and the first capillary groove, and
wherein the aerosol substrate in the first capillary groove enters the second capillary groove after converging in the gap.

8. The vaporization device of claim 7, wherein widths of the first capillary groove and the second capillary groove are less than 1 mm.

9. The vaporization device of claim 7, wherein the first capillary groove and the second capillary groove extend in a direction toward the air outlet channel.

10. The vaporization device of claim 7, wherein the first capillary groove and the second capillary groove extend in a direction toward the air outlet.

11. The vaporization device of claim 6, wherein a second capillary liquid absorbing structure extending to the vaporization cavity is provided on an inner wall of the air outlet channel so as to guide the aerosol substrate condensing on the inner wall of the air outlet channel to the vaporization cavity.

12. The vaporization device of claim 11, wherein a part of the second capillary liquid absorbing structure is in communication with the first capillary liquid absorbing structure arranged on the part of the inner wall of the vaporization cavity connected to the inner wall of the air outlet channel, and
wherein a remaining part of the second capillary liquid absorbing structure and the part of the first capillary liquid absorbing structure arranged on the part of the inner wall of the vaporization cavity connected to the inner wall of the air outlet channel are arranged at intervals.

13. The vaporization device of claim 6, wherein a tapered channel is provided in the part of the vaporization cavity in communication with the air outlet channel, and
wherein a cross-sectional area of the tapered channel gradually decreases in a direction toward the air outlet channel.

14. The vaporization device of claim 13, wherein the first capillary liquid absorbing structure arranged on the part of the inner wall of the vaporization cavity connected to the inner wall of the air outlet channel is at least partially located on the inner wall of the tapered channel.

15. The vaporization device of claim 1, wherein the vaporization assembly comprises a porous heating body.

16. The vaporization device of claim 15, wherein the porous heating body comprises a porous ceramic heating body.

17. A vaporization device, comprising:
a first carrier;
a second carrier;
an air inlet;
an air outlet;
a vaporization cavity in communication with the air inlet, a vaporization assembly being arranged in the vaporization cavity;
an air outlet channel connecting the vaporization cavity to the air outlet;
a first capillary liquid absorbing structure arranged on a part of an inner wall of the vaporization cavity close to the vaporization assembly; and
a second capillary liquid absorbing structure arranged on an inner wall of the air outlet channel so as to guide aerosol substrate condensing on the inner wall of the air outlet channel to the vaporization cavity,
wherein the first carrier and the second carrier are docked to form the vaporization cavity,
wherein the air inlet is provided on the first carrier,
wherein the vaporization assembly is arranged on the second carrier, and
wherein the first capillary liquid absorbing structure is arranged on an inner wall of the second carrier.

18. The vaporization device of claim 17, wherein the first capillary liquid absorbing structure and the second capillary liquid absorbing structure are arranged at intervals.

19. A vaporization device, comprising:

a first carrier;

a second carrier;

an air inlet;

an air outlet;

a vaporization cavity in communication with the air inlet and the air outlet, a vaporization assembly being arranged in the vaporization cavity; and a first capillary liquid absorbing structure arranged on a part of an inner wall of the vaporization cavity close to the vaporization assembly, wherein the first capillary liquid absorbing structure comprises a first capillary groove on a lower portion of the inner wall of the vaporization cavity, and a second capillary groove on an upper portion of the inner wall of the vaporization cavity, and wherein the first capillary groove and the second capillary groove define a gap therebetween, wherein the first carrier and the second carrier are docked to form the vaporization cavity, wherein the air inlet is provided on the first carrier, wherein the vaporization assembly is arranged on the second carrier, and wherein the first capillary liquid absorbing structure is arranged on an inner wall of the second carrier.

* * * * *